United States Patent [19]

Laffan

[11] Patent Number: 5,200,531
[45] Date of Patent: Apr. 6, 1993

[54] PROCESS FOR THE PRODUCTION OF THREO-4-ALKOXY-5-(ARYLHYDROXYMETHYL)-2(5H)-FURANONES

[75] Inventor: David Laffan, Visp, Switzerland

[73] Assignee: Lonza Ltd., Gampel/Valais, Switzerland

[21] Appl. No.: 808,761

[22] Filed: Dec. 17, 1991

[30] Foreign Application Priority Data

Dec. 20, 1990 [CH] Switzerland .......................... 4056/90

[51] Int. Cl.$^5$ .......................................... C07D 307/32
[52] U.S. Cl. ..................................................... 549/313
[58] Field of Search .......................................... 549/313

[56] References Cited

U.S. PATENT DOCUMENTS 4,855,320 8/1989 Chatterjee et al. ................. 514/473

FOREIGN PATENT DOCUMENTS 2845037 7/1980 Fed. Rep. of Germany .
3615157 1/1987 Fed. Rep. of Germany .

OTHER PUBLICATIONS

Pelter et al., Tetrahedron Letters, No. 18, (1970, pp. 1627–1630).
Fieser, "Fieser and Fieser's Reagents For Organic Synthesis", vol. 8, (1980), p. 268.
Pelter et al., J. Chem. Soc. Perkin Trans. I, (1987), pp. 717 to 742.

Primary Examiner—C. Warren Ivy
Assistant Examiner—A. A. Owens
Attorney, Agent, or Firm—Fisher, Christen & Sabol

[57] ABSTRACT

Threo-4-alkoxy-5-(arylhydroxymethyl)-2(5H)-furanones are obtained by condensation of 4-alkoxy-2(5H)-furanones with benzaldehydes in the presence of lithium hydroxide without contamination by the corresponding erythro stereoisomers. The condensation is preferably performed in aqueous acetonitrile and the product is precipitated from the alkaline reaction mixture by the addition of water. The products that can be produced according to the process of the invention are known pharmaceutical active ingredients with anticonvulsive or antiepileptic action.

12 Claims, No Drawings

PROCESS FOR THE PRODUCTION OF THREO-4-ALKOXY-5-(ARYLHYDROXYMETHYL)-2(5H)-FURANONES

BACKGROUND OF THE INVENTION

1. Field Of The Invention

The invention relates to a process for the production of threo-4-alkoxy-5-(arylhydroxymethyl)-2(5H)-furanones of the formula:

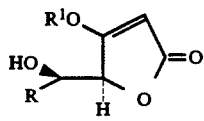
I wherein R is a phenyl group optionally substituted by one or more halogen atoms and/or lower alkyl groups and/or a nitro group and $R^1$ is an alkyl group with 1 to 4 carbon atoms. The configuration represented in formula I is to be viewed as a relative configuration; it also comprises the mirror image of the reproduced formula.

2. Background Art

Threo-4-alkoxy-5-(arylhydroxymethyl)-2(5H)-furanones are pharmaceutical active ingredients, known from West German OS 3615157, with anticonvulsive or antiepileptic activity. They were previously produced in a multistage synthesis from the enol ethers of β-oxocarboxylic acid esters, for example, (E)-3-methoxy-2-butenoic acid methyl ester, and the corresponding benzaldehydes (West German OS 3615157). This synthesis did stereospecifically yield the desired threo configuration, but it is complicated and the total yield is small.

It is known that the 5-lithio derivatives of 4-alkoxy-2(5H)-furanones (=tetronic acid alkyl esters) can be condensed with aromatic aldehydes to 4-alkoxy-5-(arylhydroxymethyl)-2(5H)-furanones [A. Pelter et al., J. Chem. Soc. Perkin Trans. I, (1987), page 717]. For the production of the 5-lithiotetronic acid esters, the tetronic acid esters were reacted with lithium diisopropylamide or n-butyllithium under protective gas at −78° C., which is hardly acceptable for a production on an industrial scale for cost and safety reasons. Also, the condensation with the aldehydes was performed under these conditions. Mixtures of threo and erythro diastereomers, whose separation is often difficult, were constantly obtained as products.

BROAD DESCRIPTION OF THE INVENTION

A main object of the invention is in particular to provide a process for the production of threo-5-(2-chlorophenyl-hydroxymethyl)-4-methoxy-2(5H)-furanones. Another main object of the invention is to provide a process for the production of 4-alkoxy-5-(arylhydroxymethyl)-2(5H)-furanones, which stereospecifically yields in high yield the threo configuration as much as possible in one stage, starting from commercially available materials, as well as without using lithium-organic reagents. Other objects and advantages are set out herein or are obvious herefrom to one skilled in the art.

The objects and advantages of the invention are achieved by the process of the invention.

The process involves a process for the production of threo-4-alkoxy-5-(arylhydroxymethyl)-2(5H)-furanones of the general formula and relative configuration:

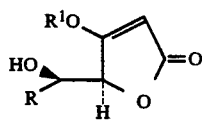
I wherein R is a phenyl group optionally substituted by one or more halogen atoms and/or lower alkyl groups and/or a nitro group and $R^1$ is an alkyl group with 1 to 4 carbon atoms. The process involves condensing a 4-alkoxy-2(5H)-furanone of the general formula:

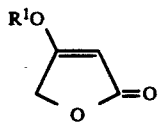
II wherein $R^1$ has the above-mentioned meaning, with an optionally substituted benzaldehyde of the general formula:

R—CHO    III wherein R has the above-mentioned meaning. The condensation is performed under catalysis by lithium hydroxide in a mixture of a dipolar aprotic solvent with a protic solvent in the volume ratio of 20:1 to 1:20. The product is precipitated by the addition of water and removal of the dipolar aprotic solvent without previous neutralization.

Preferably the volume ratio of aprotic solvent:protic solvent is 10:1 to 1:1. Preferably acetonitrile is used as the dipolar aprotic solvent and water is used as the protic solvent. Preferably the acetonitrile is removed after the addition of water by distillation under standard or reduced pressure. Advantageously the condensation is performed at a temperature of 0° to 60° C. Preferably the condensation is performed at a temperature of 10° to 40° C. Preferably in formula II $R^1$ is a methyl group. Preferably in formula III R is a 2-chlorophenyl group.

DETAILED DESCRIPTION OF THE INVENTION

It was found, surprisingly, that by using lithium hydroxide as the catalyst, 4-alkoxy-2(5H)-furanones can be condensed directly with benzaldehydes, without low temperatures, protective gas or anhydrous solvent being necessary for this purpose.

Also 4-methoxy-2(5H)-furanone recently has become commercially available - a production process is described in West German Patent No. 2,845,037. Other 4-alkoxy-2(5H)-furanones can analogously also be produced.

The reaction is suitably performed in a mixture of a dipolar aprotic solvent and a protic solvent, preferably in acetonitrile/water. The volume ratio of the aprotic to the protic solvent is advantageously between 20:1 and 1:20, preferably between 10:1 and 1:1. As the lithium hydroxide, preferably the less expensive form of monohydrate is used, the use of anhydrous lithium hydroxide provides no additional advantages. The reaction temperature is advantageously between 0° and 60° C., preferably between 10° and 40° C.

It was also found, surprisingly, that it is advantageous if, contrary to the otherwise usual mode of operation, the basic reaction mixture is not neutralized before the working up. Namely, if only water is added and the organic solvent is completely or substantially distilled off, only the desired threo diastereomer is isolated in solid form as the product. Apparently, threo and erythro diastereomers in basic solution are in equilibrium and only the slightly soluble threo diastereomer crystallizes out. On the other hand, if the reaction mixture is neutralized, the configuration equilibrium can no longer be newly adjusted, if a form crystallizes out and consequently, the erythro diastereomer resulting in the reaction cannot later be converted to the threo form.

After the product is isolated, it can be further purified in the usual way, e.g., by recrystallization.

The following examples illustrate the performance of the process according to the invention.

EXAMPLE 1

(±)-Threo-5-(2-chlorophenylhydroxymethyl)-4-methoxy-2(5H)-furanone

In 200 ml of acetonitrile, 20.0 g of 4-methoxy-2(5H)-furanone (175 mmol), 24.6 g of 2-chlorobenzaldehyde (175 mmol) and 1.47 g of lithium hydroxide-monohydrate (35.4 mmol) were dissolved at room temperature with stirring. After 30 minutes, 40 ml of water was added and, after another 60 minutes, the acetonitrile was distilled off in a vacuum at a 40° C. bath temperature. The remaining aqueous suspension was diluted with 250 ml of water and stirred for 2 hours at room temperature. The precipitated product was isolated by filtration, dried at 35° C. and 1 mbar and recrystallized from 170 ml of ethyl acetate. The product yield was 30.7 g (69.8 percent of theory). The product melting point was 149° to 150° C. Analysis of the product was:

|      |       |   |      |
| ---- | ----- | - | ---- |
| Cld. C | 56.69 | H | 4.35 |
| Fnd. C | 56.8  | H | 4.2  |

The $^1$H and $^{13}$C-NMR spectra and the chromatographic properties of the product correspond with the literature values.

EXAMPLE 2

(±)-Threo-4-methoxy-5-(phenylhydroxymethyl)-2(5H)-furanone

In 20 ml of acetonitrile, 2.0 g of 4-methoxy-2(5H)-furanone (17.5 mmol), 1.86 g of benzaldehyde (17.5 mmol) and 148 mg of lithium hydroxide monohydrate (3.5 mmol) were dissolved at room temperature with stirring. After 30 minutes, 4 ml of water was added and, after another 30 minutes, the acetonitrile was distilled off in a vacuum at a 40° C. bath temperature. The remaining aqueous suspension was diluted with 25 ml of water and stirred for 2 hours at room temperature. The precipitated product was isolated by filtration, dried at 35° C. and 1 mbar, and recrystallized from 60 ml of dichloromethane. The product yield was 2.2 g (58 percent). The product melting point was 156° to 157° C. $^1$H NMR spectrum and melting point correspond with the literature values.

What is claimed is:

1. Process for the production of a threo-4-methoxy-5-(phenylhydroxymethyl)-2(5H)-furanone of the general formula and relative configuration:

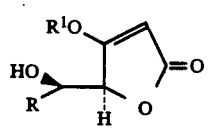

wherein R is a phenyl group optionally substituted by at least one member selected from the group consisting of a halogen atom, a lower alkyl group and a nitro group, and $R^1$ is an alkyl group with 1 to 4 carbon atoms, comprising: condensing a 4-alkoxy-2(5H)-furanone of the general formula:

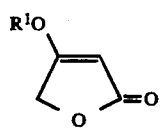

wherein $R^1$ has the above-mentioned meaning, with an optionally substituted benzaldehyde of the general formula:

R—CHO                III wherein R has the above-mentioned meaning, the condensation being performed under catalysis by lithium hydroxide at a temperature of 0° to 60° C. in a mixture of a dipolar aprotic solvent with a protic solvent in the volume ratio of 20:1 to 1:20; and precipitating the product by the addition of water without previous neutralization and removing the dipolar aprotic solvent without previous neutralization, or (2) removing the dipolar solvent without previous neutralization and precipitating the product by the addition of water without previous neutralization.

2. Process according to claim 1 wherein the volume ratio of aprotic solvent:protic solvent is 10:1 to 1:1.

3. Process according to claim 2 wherein acetonitrile is used as the dipolar aprotic solvent and water is used as the protic solvent.

4. Process according to claim 3 wherein the acetonitrile is removed after the addition of water by distillation under standard or reduced pressure.

5. Process according to claim 4 wherein the condensation is performed at a temperature of 10° to 40° C.

6. Process according to claim 5 wherein $R^1$ is a methyl group.

7. Process according to claim 6 wherein R is a 2-chlorophenyl group.

8. Process according to claim 1 wherein acetonitrile is used as the dipolar aprotic solvent and water is used as the protic solvent.

9. Process according to claim 8 wherein the acetonitrile is removed after the addition of water by distillation under standard or reduced pressure.

10. Process according to claim 9 wherein the condensation is performed at a temperature of 10° to 40° C.

11. Process according to claim 1 wherein $R^1$ is a methyl group.

12. Process according to claim 1 wherein R is a 2-chlorophenyl group.

* * * * *